(12) United States Patent
Kobayashi et al.

(10) Patent No.: US 11,471,043 B2
(45) Date of Patent: Oct. 18, 2022

(54) SUBJECTIVE OPTOMETRY APPARATUS

(71) Applicant: NIDEK CO., LTD., Gamagori (JP)

(72) Inventors: Toshihiro Kobayashi, Aichi (JP); Yukito Hirayama, Aichi (JP); Ryoji Suzuki, Aichi (JP); Kazunori Shibata, Aichi (JP); Daisuke Baba, Aichi (JP)

(73) Assignee: NIDEK CO., LTD., Aichi (JP)

(*) Notice: Subject to any disclaimer, the term of this patent is extended or adjusted under 35 U.S.C. 154(b) by 160 days.

(21) Appl. No.: 16/622,126

(22) PCT Filed: Jun. 6, 2018

(86) PCT No.: PCT/JP2018/021774
§ 371 (c)(1),
(2) Date: Dec. 12, 2019

(87) PCT Pub. No.: WO2018/230420
PCT Pub. Date: Dec. 20, 2018

(65) Prior Publication Data
US 2020/0221943 A1    Jul. 16, 2020

(30) Foreign Application Priority Data

Jun. 15, 2017 (JP) .............................. JP2017-117407

(51) Int. Cl.
*A61B 3/032* (2006.01)
*A61B 3/00* (2006.01)
*A61B 3/08* (2006.01)

(52) U.S. Cl.
CPC ............ *A61B 3/032* (2013.01); *A61B 3/0075* (2013.01); *A61B 3/08* (2013.01)

(58) Field of Classification Search
CPC ........... G02B 3/02; G02B 3/028; G02B 3/032
(Continued)

(56) References Cited

U.S. PATENT DOCUMENTS 1,469,411 A * 10/1923 Armbruster .............. A61B 3/02
                                                            351/211
4,395,097 A *  7/1983 Mohrman ............ A61B 3/0083
                                                            351/201
(Continued)

FOREIGN PATENT DOCUMENTS

CN          1585617 A      2/2005
CN        103565397 A      2/2014
(Continued)

OTHER PUBLICATIONS

Communication dated Jul. 21, 2021 issued by the Korean Intellectual Property Office in counterpart Korean Application No. 10-2019-7036961.

(Continued)

*Primary Examiner* — Zachary W Wilkes
(74) *Attorney, Agent, or Firm* — Sughrue Mion, PLLC

(57) ABSTRACT

A subjective optometry apparatus has a projection optical system including a visual target presenting portion and an optical member to project a target light flux toward a subject eye, and causing the target light flux to be incident on the optical member with a deviation of the incident target light flux from an optical axis of the optical member, a housing accommodating the projection optical system, a presentation window for emitting the target light flux from the inside of the housing to the outside thereof, an eye refractive power measurement unit provided outside the housing, and holding means integrally connecting the housing to the eye refractive power measurement unit to hold the eye refractive power measuring unit. When using the eye refractive power measuring unit, a distance from the presentation window to the eye refractive power measurement unit in an optical path is equal to or less than 180 mm.

11 Claims, 10 Drawing Sheets

(58) Field of Classification Search
USPC .................................................. 351/237, 244
See application file for complete search history.

(56) References Cited

U.S. PATENT DOCUMENTS

| | | | | |
|---|---|---|---|---|
| 4,753,527 | A * | 6/1988 | Ishihara | A61B 3/18 351/239 |
| 5,444,504 | A * | 8/1995 | Kobayashi | A61B 3/028 351/237 |
| 5,629,748 | A * | 5/1997 | Hayashi | A61B 3/032 351/232 |
| 5,989,194 | A * | 11/1999 | Davenport | A61B 3/14 600/558 |
| 10,299,672 | B2 * | 5/2019 | Shibata | A61B 3/152 |
| 2005/0018132 | A1 | 1/2005 | Fukuma et al. | |
| 2014/0185012 | A1 * | 7/2014 | Kanazawa | A61B 3/032 351/237 |
| 2015/0342455 | A1 * | 12/2015 | Kanazawa | A61B 3/032 351/243 |
| 2015/0374224 | A1 | 12/2015 | Baranton et al. | |
| 2016/0345824 | A1 * | 12/2016 | Sakurada | A61B 3/103 |
| 2020/0037869 | A1 * | 2/2020 | Hirayama | A61B 3/028 |
| 2020/0100666 | A1 * | 4/2020 | Takii | A61B 3/156 |

FOREIGN PATENT DOCUMENTS

| | | |
|---|---|---|
| CN | 103565398 A | 2/2014 |
| CN | 104427924 A | 3/2015 |
| EP | 2 949 266 A1 | 12/2015 |
| EP | 3 329 835 A1 | 6/2018 |
| JP | 4-347125 A | 12/1992 |
| JP | 5-176893 A | 7/1993 |
| JP | 7-136112 A | 5/1995 |
| JP | 07194540 A * | 8/1995 |
| JP | 9-253049 A | 9/1997 |
| JP | 2013-048753 A | 3/2013 |
| JP | 2014-128314 A | 7/2014 |
| JP | 2014128314 A * | 7/2014 |

OTHER PUBLICATIONS

Communication dated Dec. 4, 2019 issued by the State Intellectual Property Office of P.R. China in counterpart Chinese Application No. 201880004959.9.

Extended European Search Report dated Jan. 26, 2021, issued by the European Patent Office in the corresponding European Patent Application No. 18818225.7.

International Search Report (PCT/ISA/210), issued by International Searching Authority in corresponding International Application No. PCT/JP2018/021774, dated Jul. 31, 2018.

Written Opinion (PCT/ISA/237) issued by the International Searching Authority in corresponding International Application No. PCT/JP2018/021774, dated Jul. 31, 2018.

* cited by examiner

SUBJECTIVE OPTOMETRY APPARATUS

TECHNICAL FIELD

The present disclosure relates to a subjective optometry apparatus which measures optical characteristics of a subject eye.

BACKGROUND ART

A subjective optometry apparatus for examining (measuring) a refractive power and the like of a subject eye by disposing optical elements, such as a spherical lens or a cylindrical (astigmatic) lens, in an examination window of an eye refractive power measurement unit and by presenting a visual target to the subject eye through the disposed optical elements, using the eye refractive power measurement unit disposed in front of the eyes of an examinee, is known (refer to Patent Literature 1). At this time, the examinee confirms the appearance of the presented visual target by looking into the examination window of the eye refractive power measurement unit. Further, in recent years, as the subjective optometry apparatus, a subjective optometry apparatus considering space saving by shortening a distance between an eye refractive power measurement unit and a housing that accommodates a projection optical system having a visual target presenting portion has been studied.

CITATION LIST

Patent Literature

Patent Literature 1: JP-A-H05-176893

SUMMARY OF INVENTION

Incidentally in an optical store, a hospital, or the like, there is a case where the room where the subjective optometry apparatus is installed is small, and when the subjective optometry apparatus is disposed, there is a case where there is no room space. Therefore, a subjective optometry apparatus that can be disposed in a small space is desired. Thus, a subjective optometry apparatus considering space saving by reducing the distance between the eye refractive power measurement unit and the housing that accommodates the projection optical system having the visual target presenting portion has been studied. However, due to space saving, there is a problem regarding distortion of a visual target image and a problem that a target light flux cannot be projected excellently onto the subject eye because the target light flux is lost while being guided to the subject eye.

In view of the above-described related art, an object of the present disclosure is to provide a subjective optometry apparatus capable of performing a highly accurate subjective examination eyen in a case where the subjective optometry apparatus has achieved space saving.

In order to solve the above-described problem, the present invention includes the following configurations.

(1) According to a first aspect of the present disclosure, there is provided a subjective optometry apparatus including: a projection optical system that includes a visual target presenting portion which emits a target light flux and an optical member which guides an image of the target light flux to the subject eye so as to have an optically predetermined examination distance, that causes the target light flux emitted from the visual target presenting portion to be incident on the optical member with a deviation of the incident target light flux from an optical axis of the optical member, and that projects the target light flux toward the subject eye; a housing that accommodates the projection optical system; a presentation window provided on the housing to emit the target light flux from an inside of the housing to an outside of the housing therethrough; an eye refractive power measurement unit provided outside the housing to change optical characteristics of the target light flux emitted from the housing; and holding means that integrally connects the housing and the eye refractive power measurement unit to hold the eye refractive power measurement unit, in which the target light flux through the eye refractive power measurement unit is projected onto the subject eye to subjectively measure optical characteristics of the subject eye, and in a case of using the eye refractive power measurement unit, a first distance from the presentation window to the eye refractive power measurement unit in an optical path through which the target light flux from the visual target presenting portion is projected onto the subject eye is equal to or less than 180 mm.

DESCRIPTION OF EMBODIMENTS

<Outline>

Figure 1A:
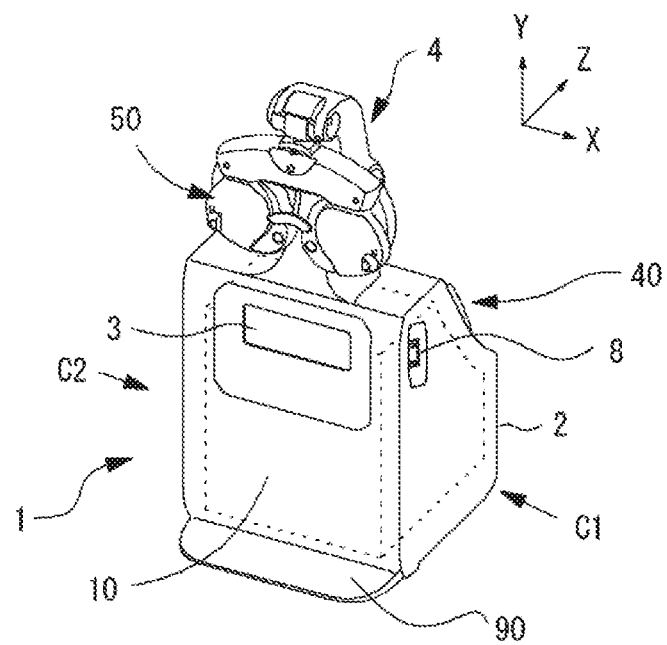
FIG. 1A is a perspective view illustrating a subjective optometry apparatus from a front left side.

Hereinafter, one of typical embodiments will be described with reference to the drawings. FIGS. 1 to 10 are views illustrating a subjective optometry apparatus according to the embodiment. In addition, items classified as the following sign "< >" may be used independently of or in relation to each other.

Further, in the following description, a description will be given on the assumption that a depth direction (a front-rear direction of an examinee when the examinee is measured) of the subjective optometry apparatus is a Z direction, a horizontal direction on a plane which is perpendicular (a left-right direction of the examinee when the examinee is measured) to the depth direction is an X direction, and a vertical direction (a vertical direction of the examinee when the examinee is measured) is a Y direction.

For example, the subjective optometry apparatus (for example, subjective optometry apparatus 1) of the present embodiment may include a projection optical system (for example, projection optical system 10) that includes a visual target presenting portion (for example, display 11) which emits a target light flux and an optical member (for example, concave mirror 13) that guides an image of the target light flux to the subject eye so as to have an optically predetermined examination distance, that causes the target light flux emitted from the visual target presenting portion to be incident on the optical member with a deviation of the incident target light flux from an optical axis of the optical member, and that projects the target light flux toward the subject eye.

For example, the subjective optometry apparatus may include a housing (for example, housing 2) that accommodates the projection optical system. For example, the subjective optometry apparatus may include a presentation window (for example, presentation window 3) provided on the housing to emit the target light flux from the inside of the housing to the outside of the housing therethrough. For example, the subjective optometry apparatus may include an eye refractive power measurement unit (for example, eye refractive power measurement unit 50) that changes optical characteristics of the target light flux emitted from the housing. For example, the eye refractive power measurement unit may be provided outside the housing.

For example, the subjective optometry apparatus may include holding means (for example, holding arm 35) that integrally connects the housing and the eye refractive power measurement unit to hold the eye refractive power measurement unit. For example, the holding means may integrally connect the eye refractive power measurement unit to an upper surface of the housing. It is needless to say that the holding means may be configured to integrally connect the housing and the eye refractive power measurement unit at a position different from the above-described position.

For example, in a case of using the eye refractive power measurement unit (for example, in a case where the eye refractive power measurement unit is disposed in the examination position), an examination window (for example, examination window 53) of the eye refractive power measurement unit and the presentation window of the housing may be configured to be disposed to face each other.

For example, the subjective optometry apparatus of the present embodiment is used for projecting the target light flux through the eye refractive power measurement unit onto the subject eye to subjectively measure optical characteristics of the subject eye by. Examples of the optical characteristics of the subject eye which is subjectively measured include an eye refractive power (for example, a spherical power, an astigmatic power, an astigmatic axis angle, and the like), a contrast sensitivity, a binocular visual function (for example, an amount of oblique position, a stereoscopic function, and the like), and the like.

For example, in the subjective optometry apparatus, in a case of using the eye refractive power measurement unit (for example, in a case where the eye refractive power measurement unit is disposed in the examination position), a first distance (for example, distance W) from the presentation window of the housing to the eye refractive power measurement unit in an optical path through which the target light flux from the visual target presenting portion is projected onto the subject eye may be equal to or less than 180 mm. In other words, for example, the first distance in a depth direction (Z direction) from the presentation window to the eye refractive power measurement unit in the optical path through which the target light flux from the visual target presenting portion is projected onto the subject eye may be equal to or less than 180 mm (for example, 70 mm, 66 mm, 50 mm, 10 mm, and the like). For example, the first distance may be a distance from the presentation window of the housing to the examination window of the eye refractive power measurement unit. In addition, the examination window of the eye refractive power measurement unit may be an examination window (for example, examination window 53b) on the examinee side or an examination window (for example, examination window 53a) on the housing side. In addition, in the present embodiment, a case where the first distance is equal to or less than 180 mm includes a configuration in which the first distance is approximately equal to or less than 180 mm.

For example, since the first distance is set to be equal to or less than 180 mm, the subjective optometry apparatus may have a configuration in which the holding means connects the eye refractive power measurement unit and the housing at 180 mm or less. For example, since the first distance is set to be equal to or less than 180 mm, the subjective optometry apparatus may have a configuration in which the holding means connects the eye refractive power measurement unit and the housing at 180 mm or less.

In this manner, for example, the subjective optometry apparatus includes the projection optical system that includes the visual target presenting portion which emits the target light flux and the optical member that guides the image of the target light flux to the subject eye so as to have an optically predetermined examination distance, that causes the target light flux emitted from the visual target presenting portion to be incident on the optical member with a deviation of the incident target light flux from the optical axis of the optical member, and that projects the target light flux toward the subject eye. In addition, for example, the subjective optometry apparatus is a subjective optometry apparatus including: a housing that accommodates the projection optical system; a presentation window provided on the housing to emit the target light flux from the inside of the housing to the outside of the housing therethrough; an eye refractive power measurement unit provided outside the housing to change optical characteristics of the target light flux emitted from the housing; and holding means that integrally connects the housing and the eye refractive power measurement unit to hold the eye refractive power measurement unit, in which the target light flux through the eye refractive power measurement unit is projected onto the subject eye to subjectively measure the optical characteristics of the subject eye. Further, for example, in the subjective optometry apparatus, in a case of using the eye refractive power measurement unit, a first distance from the presentation window to the eye refractive power measurement unit in an optical path through which the target light flux from the visual target presenting portion is projected onto the subject eye is equal to or less than 180 mm. With such a configuration, it is possible to save the space for the subjective optometry apparatus, and to perform a highly accurate subjective examination eyen in a case of the subjective optometry apparatus in which the eye refractive power measurement unit and the housing are integrated with each other.

Further, for example, in the subjective optometry apparatus, in a case of using the eye refractive power measurement unit, the first distance from the presentation window of the housing to the eye refractive power measurement unit in the optical path through which the target light flux from the visual target presenting portion is projected onto the subject eye may be equal to or greater than 10 mm. In other words, the first distance may be any distance between 10 mm and 180 mm. For example, since the space is generated between the eye refractive power measurement unit and the housing by setting the first distance to be equal to or greater than 10 mm, when the eye refractive power measurement unit is moved (for example, when the eye refractive power measurement unit is moved between the examination position and the retracted position), it is possible to suppress interference between the eye refractive power measurement unit and the housing.

For example, in the subjective optometry apparatus, the visual target presenting portion and the optical member may be disposed such that a second distance (for example distance W1+W2) from the visual target presenting portion to the optical member in the optical path is any distance between 540 mm and 570 mm (for example, 550 mm, 555 mm, 560 mm, and the like), in order to enable to subjectively measure the optical characteristics of the subject eye with the first distance. In other words, the second distance may be set corresponding to the first distance. In this manner, for example, the visual target presenting portion and the optical member may be disposed such that the second distance from the visual target presenting portion to the optical member to the visual target presenting portion in the optical path through which the target light flux from the visual target presenting portion is projected onto the subject eye is any distance between 540 mm and 570 mm, in order to enable to subjectively measure the optical characteristics of the subject eye with the first distance. Accordingly, it is possible to save the space for the subjective optometry apparatus and to perform a highly accurate subjective examination.

For example, as a configuration in which the optical characteristics of the subject eye are subjectively measurable at the first distance, the subjective optometry apparatus may have a configuration in which the visual target can be seen to be presented at a position of 5 m with respect to the subject eye (a virtual image can be formed at an image point position of 5 m from the subject eye) in a far distance examination. In addition, for example, as a configuration in which the optical characteristics of the subject eye are subjectively measurable at the first distance, the subjective optometry apparatus may have a configuration in which the target light flux emitted from the visual target presenting portion is projected onto the subject eye in a state where the distortion is small. Further, for example, as a configuration in which the optical characteristics of the subject eye are subjectively measurable at the first distance, the subjective optometry apparatus may have a configuration in which the subjective optometry apparatus can save the space.

For example, as a space-saving subjective optometry apparatus, in a state where the eye refractive power measurement unit is disposed in the examination position, the size (length from a rear surface of the housing to a front surface (front surface of the eye refractive power measurement unit on the examinee side) of the eye refractive power measurement unit) in the depth direction may be equal to or less than 550 mm (for example, 540 mm, 519 mm, 510 mm, and the like), the size (length) in the horizontal direction (X direction) may be equal to or less than 570 mm (for example, 560 mm, 550 mm, 540 mm, and the like), and the size (length) in the vertical direction (Y direction) may be equal to or less than 780 mm (770 mm, 763 mm, 750 mm, and the like). It is needless to say that the space-saving subjective optometry apparatus is not limited to the above-described size.

In addition, for example, in the subjective optometry apparatus, a curvature of the optical member that corresponds to the second distance may be set. For example, a configuration in which, as the curvature of the optical member, a focal distance of the optical member is any focal distance between 620 mm and 650 mm may be employed. It is needless to say that the curvature of the optical member is not limited to the above-described focal distance. In this manner, for example, by setting the curvature of the optical member that corresponds to the second distance, eyen in a case where the second distance differs depending on the projection optical system, the visual target can be presented at a predetermined magnification.

For example, the optical member that guides the image of the target light flux to the subject eye so as to have an optically predetermined examination distance may be at least one of a concave mirror and a lens. For example, in a case where the optical member is a concave mirror, an incident angle of the target light flux to the concave mirror may be equal to or less than 10°. In this case, for example, the visual target presenting portion and the concave mirror may be disposed such that the incident angle of the target light flux to the concave mirror is equal to or less than 10°. In addition, the incident angle may be an angle formed by an axis (optical axis of the visual target presenting portion) in a normal direction with respect to a screen of the visual target presenting portion and an optical axis of the concave mirror. In this manner, f example, in the present example, the optical member may be a concave mirror, and the incident angle of the target light flux to the concave mirror may be equal to or less than 10°. Accordingly, distortion or aberration due to the concave mirror can be suppressed, and a highly accurate subjective examination can be performed.

For example, in the subjective optometry apparatus, the presentation window may have a size of 130 mm or more in a horizontal direction and a size of 50 mm or more in a vertical direction, in order to enable to subjectively measure the optical characteristics of the subject eye with the first distance. In this case, as an example, a viewing angle when an examiner looks into the examination window may be 40°. It is needless to say that different viewing angles may be used. In this case, as an example, the distance (PD) between the optical axes of the left and right examination windows of the eye refractive power measurement unit may be 85 mm. It is needless to say that the PD may be a different distance. In this manner, for example, in the subjective optometry apparatus, the presentation window may have a size of 130 mm or more in the horizontal direction and a size of 50 mm or more in the vertical direction, in order to enable to subjectively measure the optical characteristics of the subject eye with the first distance. Accordingly, in a case of an integrated subjective optometry apparatus, when the examinee observes the visual target presenting portion through an optometric window, narrowing of the viewing angle when looking into the optometric window is suppressed, and preferably, the subjective examination can be performed. In addition, when the visual target presenting portion is observed through the optometric window, as a frame or the like of the presentation window is seen, the action of an adjustment force of the subject eye can be suppressed, and a highly accurate subjective examination can be performed.

In addition, in the present embodiment, a case where the size of the presentation window in the horizontal direction is equal to or greater than 130 mm and the size of the presentation window in the vertical direction is equal to or greater than 50 mm has been described as an example, but the present invention is not limited thereto. For example, the presentation window may have the size wider than the range of the viewing angle (for example, the viewing angle of the examination window) when the examinee looks into the examination window. In other words, any configuration may be employed as long as the frame of the presentation window deviates from the viewing angle. In addition, the size of the visual target presenting portion may be changed corresponding to the size of the presentation window.

For example, in the subjective optometry apparatus, the presentation window may have a size of 270 mm or less in the horizontal direction and a size of 190 mm or less in the vertical direction, in order to enable to subjectively measure the optical characteristics of the subject eye with the first distance. Accordingly, in a case of an integrated subjective optometry apparatus, when the visual target presenting portion is observed through the optometric window, as the disturbance light reflected by the presentation window is guided to the subject eye and the disturbance light enters the housing, difficulty in confirming the visual target can be suppressed and a highly accurate subjective examination can be performed. In addition, the size of the visual target presenting portion may be changed corresponding to the size of the presentation window.

<Projection Optical System>

For example, the projection optical system may include at least one or more optical members that project the target light flux toward the subject eye.

For example, in the projection optical system, the target light flux emitted from the visual target presenting portion to be incident on the optical member is deviated from the optical axis of the optical member, and the target light flux is projected toward the subject eye. In this case, for example, the visual target presenting portion may be disposed by tilting the normal direction to the screen of the visual target presenting portion with respect to the optical axis of the optical member.

For example, in a case where the optical member is a concave mirror, the projection optical system may include a reflection member (for example, flat surface mirror 12) which reflects the target light flux emitted by the visual target presenting portion toward the concave mirror and guides the target light flux reflected by the concave mirror from the inside of the housing to the outside of the housing. With such a configuration, it is possible to reduce the number of members of the projection optical system and to save the space of the subjective optometry apparatus. It is needless to say that the projection optical system is not limited to the above-described configuration, and a configuration in which the target light flux emitted from the visual target presenting portion to be incident on the optical member is deviated from the optical axis of the optical member and the target light flux is projected toward the subject eye may be employed.

For example, the reflection member may be any one of a mirror (for example, a total reflection mirror, a half mirror, and the like), a prism, and the like. It is needless to say that the reflection member is not limited thereto, and a member that guides the target light flux toward the subject eye may be employed.

For example, a tilt angle of the reflection member may be any tilt angle between 30° and 40° (for example, 34°, 36°, 38°, and the like). As the tilt angle of the reflection member is designed at any tilt angle between 30° and 40°, the subjective optometry apparatus can further save the space. It is needless to say that the tilt angle of the reflection member is not limited thereto, and may be designed with various tilt angles. In addition, the tilt angle of the reflection member may be a tilt angle with respect to the optical axis (optical axis set for projecting the visual target from a front direction with respect to the subject eye) (for example, optical axis L4) through which the target light flux reflected by the reflection member is oriented toward the subject eye. For example, the tilt angle of the reflection member may be an angle formed by the optical axis through which the target light flux reflected by the reflection member is oriented toward the subject eye and the optical axis (axis in the normal direction of the reflection surface of the reflection member) of the reflection member.

For example, a configuration may also be employed in which a display is used as the visual target presenting portion. For example, a liquid crystal display (LCD), an organic electroluminescence (EL), or the like is used as the display. For example, an examination visual target, such as a Landolt ring visual target, is displayed on the display. For example, a digital micromirror device (DMD) may be used as the visual target presenting portion. In general, the DMD has high reflectivity and luminance. Therefore, it is possible to maintain the quantity of light of the target light flux compared to a case where a liquid crystal display using polarization is used.

For example, as the visual target presenting portion, a configuration including a visual target presenting visible light source and a visual target plate may be employed. In this case, for example, the visual target plate is a rotatable disk plate, and includes a plurality of visual targets. The plurality of visual targets include, for example, a visual target for examination of visual acuity which is used during the subjective measurement, and the like. For example, regarding the visual target for examination of visual acuity, a visual target (visual acuity value 0.1, 0.3, . . . , and 1.5) is provided for each visual acuity value. For example, the visual target plate is rotated by a motor or the like, and the visual targets are disposed in a switching manner in the optical path through which the target light flux is guided to the subject eye. It is needless to say that a visual target presenting portion other than the above-described configuration may be used as the visual target presenting portion that projects the target light flux.

For example, in the present embodiment, the projection optical system may include a right eye projection optical system and a left eye projection optical system which are provided as a pair on the left and right sides. In this case, for example, a visual target presenting portion provided as a pair on the left and right sides may be used. For example, the right eye projection optical system and the left eye projection optical system may be configured such that members configuring the right eye projection optical system and members configuring the left eye projection optical system are configured with the same member. In addition, for example, the right eye projection optical system and the left eye projection optical system may be configured such that at least a part of the members configuring the right eye projection optical system and the members configuring the left eye projection optical system are configured with different members. For example, the right eye projection optical system and the left eye projection optical system may be configured such that at least a part of the members configuring the right eye projection optical system and the members configuring the left eye projection optical system are used in common. In addition, for example, the right eye projection optical system and the left eye projection optical system may be configured such that the members configuring the right eye projection optical system and the members configuring the left eye projection optical system are separately provided.

<Eye Refractive Power Measurement Unit>

For example, the eye refractive power measurement unit may change the optical characteristics (for example, at least any one of a spherical power, a cylindrical power, a cylindrical axis, polarization characteristics, and the aberration amount) of the target light flux. For example, as a configuration in which the optical characteristics of the target light flux is changed, a configuration in which an optical element is controlled may be employed. For example, the eye refractive power measurement unit may have a configuration using a wavefront modulation element. For example, the eye refractive power measurement unit may be configured to include a pair of left and right lens chamber units for switching and disposing the optical elements in the examination window.

<Moving Means>

For example, the subjective optometry apparatus may include moving means (for example, moving unit 6). For example, the moving means may be configured to include driving means (for example, driving portion 30) for moving the position of the eye refractive power measurement unit, and enable the eye refractive power measurement unit to move between the examination position in front of the subject eye and the retracted position by driving the driving means. For example, the subjective optometry apparatus may include control means (for example, control portion 80). For example, the control means may control the moving means by driving the driving means, and may move the eye refractive power measurement unit between the examination position in front of the subject eye and the retracted position.

For example, the eye refractive power measurement unit can be easily moved by automatically moving the eye refractive power measurement unit between the examination position in front of the subject eye and the retracted position.

For example, the moving means may be configured to enable move the eye refractive power measurement unit to move to the retracted position where is above the examination position. Accordingly, since the eye refractive power measurement unit can be retracted without crossing the face of the examinee, it is possible to provide a subjective optometry apparatus that can further suppress excessive contact. Moreover, even when other members are disposed around the subjective optometry apparatus, it is possible to suppress the possibility that the eye refractive power measurement unit is in excessive contact with the other members.

Further, for example, the moving means may be configured to enable move the eye refractive power measurement unit to move to the retracted position in the horizontal direction (for example, at least one of the left direction and the right direction) from the examination position. It is needless to say that, for example, the moving means may be configured to enable the eye refractive power measurement unit to move to the retracted position in any direction from the examination position.

In addition, in the present example, a configuration in which the eye refractive power measurement unit can be moved between the examination position in front of the subject eye and the retracted position by driving the driving means has been described, but the present invention is not limited thereto. For example, the eye refractive power measurement unit may be configured to be manually moved.

Example

Figure 1B:
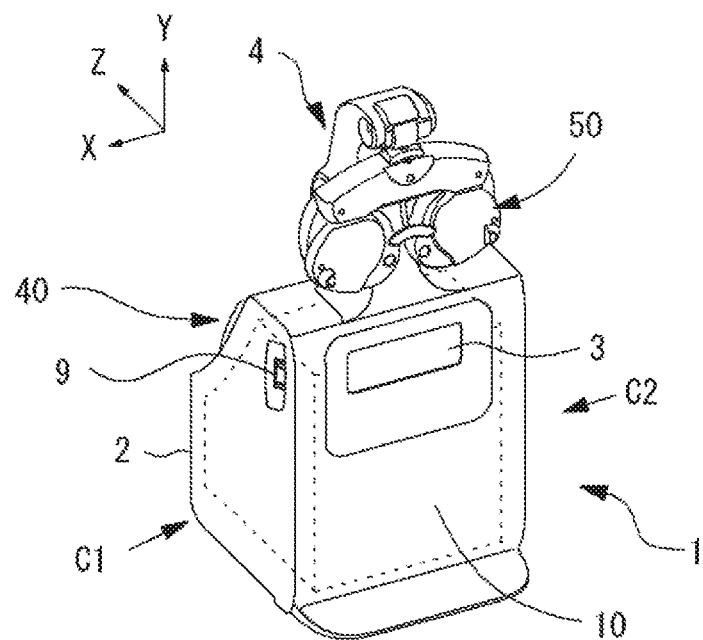
FIG. 1B is a perspective view illustrating the subjective optometry apparatus from a front right side.
Figure 2:
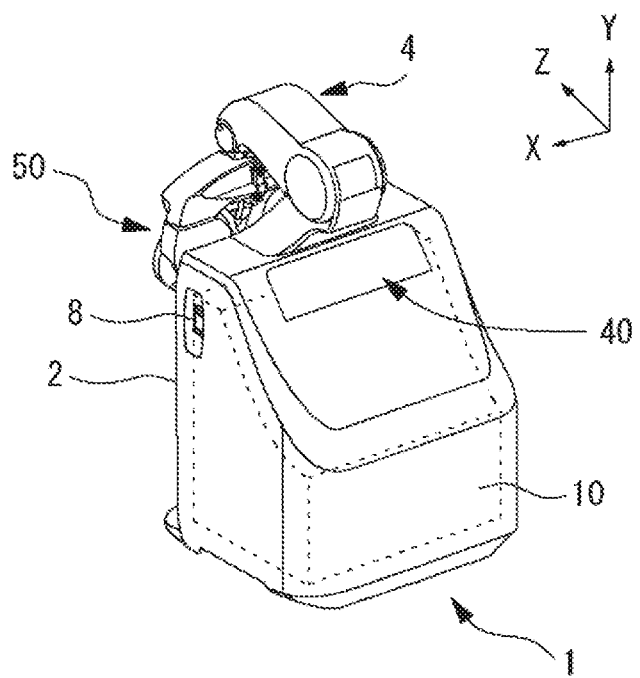
FIG. 2 is a perspective view illustrating the subjective optometry apparatus from a rear side.

Hereinafter, the configuration of the subjective optometry apparatus in the present example will be described. For example, FIGS. 1A and 1B are perspective views illustrating the subjective optometry apparatus 1 from a front side. For example, FIG. 2 is a perspective view illustrating the subjective optometry apparatus 1 according to the present example from a rear surface side. In addition, in the present example, the side on which the presentation window 3 which will be described later is positioned will be described as the front surface of the subjective optometry apparatus 1, and the side on which an observation window 41 which will be described later is positioned will be described as the rear surface of the subjective optometry apparatus 1. For example, FIG. 1A is a perspective view illustrating the subjective optometry apparatus 1 from the front left side. In addition, for example, FIG. 1B is a perspective view illustrating the subjective optometry apparatus 1 from the front right side.

For example, the subjective optometry apparatus 1 includes the housing 2, the presentation window 3, a holding unit 4, a first operation portion 8, a second operation portion 9, the projection optical system 10, an observation unit 40, the eye refractive power measurement unit 50, and the like. In addition, in the present example, the subjective optometry apparatus 1 is provided with an elbow rest 90. For example, since the elbow rest 90 is provided, the examination can be performed in a stable state. For example, even in a case where the examiner performs the examination while standing, the examination can be performed in a state where the elbow is placed on the elbow rest 90, and accordingly, the examination can be performed by stabilizing the posture, and a highly accurate subjective examination can be performed. In addition, an arm for the examinee to grip with hand may further be provided in the elbow rest 90. By placing the elbow on the elbow rest 90 and gripping the arm with hand, the examination can be performed by stabilizing the posture.

For example, in the present example, the examinee faces the front surface of the housing 2. For example, the housing 2 accommodates the projection optical system 10 therein. For example, the presentation window 3 is used for presenting the examination visual target to the eyes of the examinee (hereinafter, referred to as a subject eye). For example, the presentation window 3 transmits the target light flux in the projection optical system 10. Therefore, the target light flux via the presentation window 3 is projected onto the subject eye. For example, the presentation window 3 is closed with a transparent panel in order to prevent invasion of dust or the like. For example, as a transparent panel, a transparent member, such as an acrylic resin or a glass plate, can be used. In the present example, for example, the presentation window 3 has a size of 184 mm in the horizontal direction and a size of 99 mm in the vertical direction. It is needless to say that the size of the presentation window 3 is not limited thereto. For example, the size of the presentation window 3 in the horizontal direction may be equal to or greater than 130 mm and the size of the presentation window 3 in the vertical direction may be equal to or greater than 50 mm. In addition, for example, the size of the presentation window in the horizontal direction may be equal to or less than 270 mm and the size of the presentation window 3 in the vertical direction may be equal to or less than 190 mm.

In addition, in a case where the eye refractive power measurement unit 50 is disposed between the presentation window 3 and the subject eye, the target light flux via the presentation window 3 and the examination window 53 of the eye refractive power measurement unit 50 is projected onto the subject eye.

Figure 8:
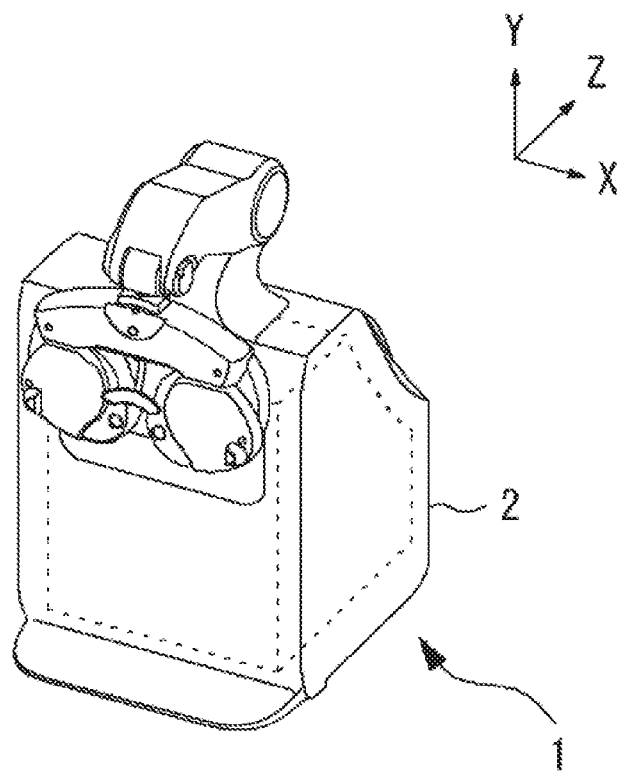
FIG. 8 is a view illustrating a state where the eye refractive power measurement unit is lowered to the front of a housing.

For example, the holding unit 4 holds the eye refractive power measurement unit 50. For example, by the holding unit 4, the eye refractive power measurement unit 50 is supported in the retracted position or in the examination position. For example, in the retracted position in the present example, as illustrated in FIGS. 1A and 1B, the eye refractive power measurement unit 50 is in a state of being raised above the housing 2. In addition, in the examination position in the present example, as illustrated in FIG. 8, the eye refractive power measurement unit 50 is in a state of being lowered in front of the housing 2. Such switching between the retracted position and the examination position is performed by vertically moving the holding arm 35 (refer to FIGS. 3A and 3B) of the holding unit 4 by a moving unit 6 (refer to FIGS. 3A and 3B) included in the holding unit 4. In addition, in the present example, the holding unit 4 in which the holding arm 35 and the moving unit 6 are integrally configured is provided. It is needless to say that the holding arm 35 and the moving unit 6 may be separately and independently provided.

<Holding Unit>

Figure 3A:
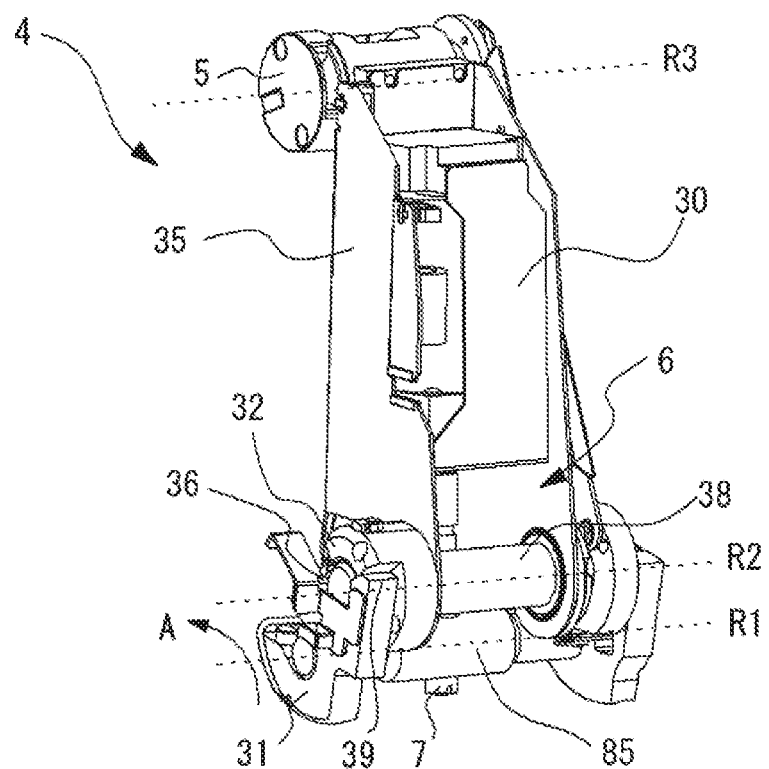
FIG. 3A illustrates an internal configuration of a holding unit in a case where the eye refractive power measurement unit is moved to a retracted position.
Figure 3B:
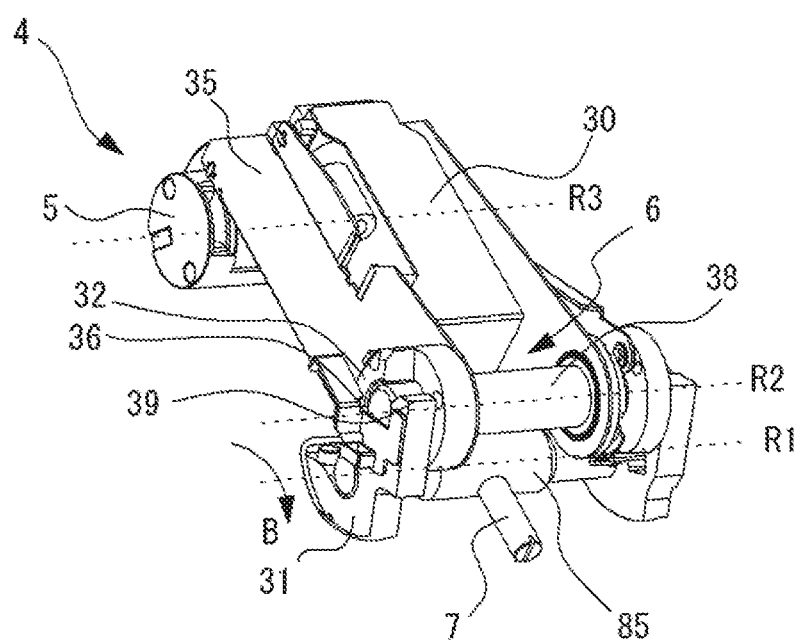
FIG. 3B illustrates an internal configuration of the holding unit in a case where the eye refractive power measurement unit is moved to an examination position.

Hereinafter, the holding unit 4 will be described in detail. For example, FIGS. 3A and 3B illustrate a schematic view of an internal configuration in a case where an external cover of the holding unit 4 is removed. In addition, in FIGS. 3A and 3B, the eye refractive power measurement unit 50 connected to the support arm 35 is omitted. For example, FIG. 3A illustrates an internal configuration of the holding unit 4 in a case where the eye refractive power measurement unit 50 is moved to the retracted position. For example, FIG. 3B illustrates an internal configuration of the holding unit 4 in a case where the eye refractive power measurement unit 50 is moved to the examination position.

For example, the holding unit 4 includes a connecting portion 5, the moving unit 6, a base 31, the holding arm 35, and the like. For example, the holding unit 4 is connected to the eye refractive power measurement unit 50 via the connecting portion 5. For example, the connecting portion 5 is rotatably connected to the holding arm 35 with a rotary axis R3 as the center. For example, the holding arm 35 is rotatably attached to the base 31. For example, the base 31 is provided on the upper surface of the housing 2. For example, the base 31 is connected to the housing 2 via the connecting portion 33. For example, the base 31 is disposed to be fixed to the housing 2 via the connecting portion 33. In addition, in the present example, a configuration in which the base 31 and the connecting portion 33 are provided separately has been described as an example, but the present disclosure is not limited thereto. The base 31 and the connecting portion 33 may be integrally configured. In this case, for example, the base 31 and the housing 2 may be connected to each other.

For example, the moving unit 6 includes a driving portion (for example, a motor) 30, a shaft 7, a supporting member 85, a block 32, a block receiver 36, a supporting member 38, a block receiver 39, a detector 70, a light shielding portion 71, a slot 72, a restriction member 75, a slot 76, a bearing 77, and the like. In addition, the moving unit 6 may be configured to include at least the motor 30. For example, the motor 30 is fixed to the holding arm 35 and is connected to the upper part of the shaft 7. For example, the lower part of the shaft 7 has a screw portion (not illustrated) and is fitted to the supporting member 85. In other words, the supporting member 85 has a screw portion (not illustrated) at the part through which the shaft 7 penetrates so as to be fitted to the shaft 7. For example, the supporting member 85 is attached to the base 31. For example, the supporting member 85 rotatably supports the shaft 7 with respect to the base 31 with a rotary axis (central axis) R1 of the supporting member 85 as the center. For example, the holding arm 35 is attached to the base 31 by the supporting member 38. For example, the supporting member 38 rotatably supports the holding arm 35 with respect to the base 31 with a rotary axis (central axis) R2 of the supporting member 38 as the center.

For example, the block 32 is connected to the supporting member 38. For example, the block 32 is rotatable with respect to the base 31 with the rotary axis R2 of the supporting member 38 as the center together with the rotation of the supporting member 38. For example, the block receiver 36 and the block receiver 39 are fixed to the base 31. For example, the block receiver 36 and the block receiver 39 are in contact with the block 32 at different predetermined positions. For example, in a case where the block 32 rotates with respect to the base 31 with the rotary axis R2 of the supporting member 38 as the center in accordance with the rotation of the supporting member 38, when the block 32 rotates to a predetermined position, the block 32 comes into contact with the block receiver 36 or the block receiver 39 provided in the base 31, and the rotation of the block 32 is stopped. For example, in the present example, in the block receiver 36, in a case where the eye refractive power measurement unit 50 reaches the examination position from the retracted position, the block receiver 36 and the block 32 come into contact with each other, and the block receiver 36 is disposed at a position at which the rotation of the block 32 is stopped. In addition, for example, in the present example, in the block receiver 39, in a case where the eye refractive power measurement unit 50 reaches the retracted position from the examination position, the block receiver 39 and the block 32 come into contact with each other, and the block receiver 39 is disposed at a position at which the rotation of the block 32 is stopped.

For example, the operation in which a state where the eye refractive power measurement unit 50 is disposed in the retracted position as illustrated in FIG. 3A becomes a state where the eye refractive power measurement unit 50 is disposed in the examination position as illustrated in FIG. 3B will be described. For example, as the motor 30 is driven, the shaft 7 rotates. For example, as the motor 30 positively rotates, the shaft 7 rotates. As the shaft 7 rotates, the screw portion of the shaft 7 rotates and moves with respect to the supporting member 85 screwed with the screw portion of the shaft 7. In other words, with respect to the supporting member 85, the shaft 7 moves in a shaft direction of the shaft 7. For example, the shaft 7 moves with respect to the supporting member 85 and the protruding part of the shaft 7 increases from the supporting member 85 (the shaft 7 becomes longer). For example, in conjunction with the movement in which the protruding part of the shaft 7 increases, the supporting member 85 rotates in an arrow A direction with the rotary axis R1 as the center.

For example, as the supporting member 85 rotates with the rotary axis R1 as the center, the shaft 7 also rotates with the rotary axis R1 as the center. In other words, the shaft 7 moves in the shaft direction of the shaft 7 with respect to the supporting member 85 and rotates in the arrow A direction with the rotary axis R1 as the center. For example, as the shaft 7 rotates, the motor 30 connected to the shaft 7 rotates in the arrow A direction with the rotary axis R1 as the center. Further, for example, the holding arm 35 to which the motor 30 is fixed rotates integrally with the rotation of the motor 30 in the arrow A direction with the rotary axis R2 of the supporting member 38 as the center. Accordingly, the connecting portion 5 connected to the holding arm 35 rotates in the arrow A direction, and the eye refractive power measurement unit 50 connected to the connecting portion 5 rotates in the arrow A direction. Further, for example, the connecting portion 5 rotates with respect to the holding arm 35 such that the eye refractive power measurement unit 50 can maintain a vertical state by the own weight of the eye refractive power measurement unit 50. In addition, in the present example, the vertical state includes a substantially vertical state. Accordingly, for example, the eye refractive power measurement unit 50 moves from the retracted position as illustrated in FIG. 3A to the examination position as illustrated in FIG. 3B. In other words, the eye refractive power measurement unit 50 can be moved downward.

Further, for example, the rotation (movement to the examination position) of the eye refractive power measurement unit 50 in the A direction is stopped when the eye refractive power measurement unit 50 reaches the examination position by the block 32 and the block receiver 36. For example, with the driving of the motor 30, the block 32 is rotated in the A direction with the rotary axis R2 as the center and comes into contact with the block receiver 36 when the eye refractive power measurement unit 50 reaches the examination position. For example, as the block 32 comes into contact with the block receiver 36, the rotation is stopped. For example, by stopping the block 32, the rotation of the supporting member 38 connected to the block 32 is stopped. In addition, according to this, the rotation of the shaft 7 and the supporting member 85 is also stopped. According to this, the eye refractive power measurement unit 50 is stopped in the examination position. In other words, the eye refractive power measurement unit 50 is stopped in the examination position by the block 32, and the block receiver 36.

For example, after the rotation movement to the examination position) of the eye refractive power measurement unit 50 in the A direction is stopped when the eye refractive power measurement unit 50 reaches the examination position by the block 32 and the block receiver 36, the motor 30 continues to be driven. For example, as the motor 30 is driven, the shaft 7 rotates, but the shaft 7 cannot be moved by the block 32 and the block receiver 36. At this time, for example, the movement of the shaft 7 in the shaft direction of the shaft 7 with respect to the supporting member 85 is stopped, and the movement of the supporting member 85 with respect to the shaft 7 is started. In other words, the driving by the motor 30 is switched from the movement of the shaft 7 to the movement of the supporting member 85. For example, after the movement of the supporting member 85 is started, when the supporting member 85 is moved to a predetermined position, the driving of the motor 30 is stopped.

In this manner, the movement of the eye refractive power measurement unit 50 to the examination position is completed. For example, the switching mechanism from the movement of the shaft 7 to the movement of the supporting member 85 can be used as a contact restraining mechanism in a case where the eye refractive power measurement unit 50 is in contact with another member when the eye refractive power measurement unit 50 is moving to the examination position.

For example, the operation in which a state where the eye refractive power measurement unit 50 is disposed in the examination position as illustrated in FIG. 3B becomes a state where the eye refractive power measurement unit 50 is disposed in the retracted position as illustrated in FIG. 3A will be described. For example, as the motor 30 negatively rotates, the shaft 7 rotates. As the shaft 7 rotates, for example, the shaft 7 moves in the shaft direction of the shaft 7 with respect to the supporting member 85 and the protruding part of the shaft 7 from the supporting member 85 decreases (the shaft 7 becomes shorter). For example, in conjunction with the movement in which the shaft 7 becomes shorter, the supporting member 85 rotates in an arrow B direction with the rotary axis R1 as the center. Similar to the description above, as the supporting member 85 rotates with the rotary axis R1 as the center, the connecting portion 5 connected to the holding arm 35 rotates in the arrow B direction with the rotary axis R2 as the center, and the eye refractive power measurement unit 50 connected to the connecting portion 5 rotates in the arrow B direction. Further, for example, the connecting portion 5 rotates with respect to the holding arm 35 such that the eye refractive power measurement unit 5 can maintain a vertical state by the own weight of the eye refractive power measurement unit 50. Accordingly, for example, the eye refractive power measurement unit 50 moves from the examination position as illustrated in FIG. 3B to the retracted position as illustrated in FIG. 3A. In other words, the eye refractive power measurement unit 50 can be moved upward.

Further, for example, the rotation (movement to the retracted position) of the eye refractive power measurement unit 50 in the B direction is stopped when the eye refractive power measurement unit 50 reaches the retracted position by the block 32 and the block receiver 39. For example, with the driving of the motor 30, the block 32 is rotated in the B direction with the rotary axis R2 as the center and comes into contact with the block receiver 39 when the eye refractive power measurement unit 50 reaches the retracted position. For example, as the block 32 comes into contact with the block receiver 39, the rotation is stopped. For example, by stopping the block 32, the rotation of the supporting member 38 connected to the block 32 is stopped. In addition, according to this, the rotation of the shaft 7 and the supporting member 85 is also stopped. According to this, the eye refractive power measurement unit 50 is stopped in the retracted position. In other words, the eye refractive power measurement unit 50 is stopped in the retracted position by the block 32 and the block receiver 39. In this manner, the movement of the eye refractive power measurement unit 50 to the retracted position is completed.

In addition, in the present example, the configuration in which the movement of the eye refractive power measurement unit 50 to the retracted position is stopped by the block 32 and the block receiver 39 has been described as an example, but the present invention is not limited thereto. For example, detection means for detecting a retracted state may be provided, and the movement of the eye refractive power measurement unit 50 to the retracted position may be stopped based on the detection result. In this case, as an example, for example, a shielding portion is provided in the supporting member 38 and a detector is provided on the base 31. For example, in a case where the eye refractive power measurement unit 50 is positioned in the retracted position, and in a case where the shielding portion provided in the supporting member 38 is detected by the detector, the movement of the eye refractive power measurement unit 50 to the retracted position may be stopped.

<First Operation Portion and Second Operation Portion>

Hereinafter, the first operation portion 8 and the second operation portion 9 will be described. For example, the first operation portion 8 is a vertical movement switch (movement switch of the eye refractive power measurement unit 50). In addition, for example, the second operation portion 9 is a vertical movement switch (movement switch of the eye refractive power measurement unit 50). In other words, in the present example, the first operation portion 8 and the second operation portion 9 are operation portions for performing the same operation. For example, by operating the first operation portion 8 or the second operation portion 9, it is possible to move the eye refractive power measurement unit 50 between the examination position in front of the subject eye and the retracted position.

For example, the first operation portion 8 is disposed on the left surface of the housing 2. For example, the second operation portion 9 is disposed on the right surface of the housing 2. For example, the first operation portion and the second operation portion are disposed above the left and right surfaces. In addition, in the present example, for example, the first operation portion and the second operation portion are disposed at laterally symmetrical positions using the center of the housing 2 as a reference.

In addition, in the present example, for example, the first operation portion 8 and the second operation portion 9 are operation portions having the same shape. For example, since the first operation portion 8 and the second operation portion 9 have the same shape, when operating one of the first operation portion 8 or the second operation portion 9, the subjective optometry apparatus 1 can be operated by the same operation as the other operation, and thus, it is possible to suppress the possibility that an examiner performs an erroneous operation and it becomes easy to perform the operation.

In addition, in the present example, a configuration in which the first operation portion 8 and the second operation portion 9 are provided as the operation portions for moving the eye refractive power measurement unit 50 between the examination position in front of the subject eye and the retracted position is employed, but the present invention is not limited thereto. For example, as the operation portion for moving the eye refractive power measurement unit 50 between the examination position in front of the subject eye and the retracted position, at least one operation portion may be provided. As an example, in a case where one operation portion is used, the operation portion may be disposed at a position where the operation from the left and right sides of the subjective optometry apparatus 1 is possible.

<Projection Optical System>

Figure 4A:
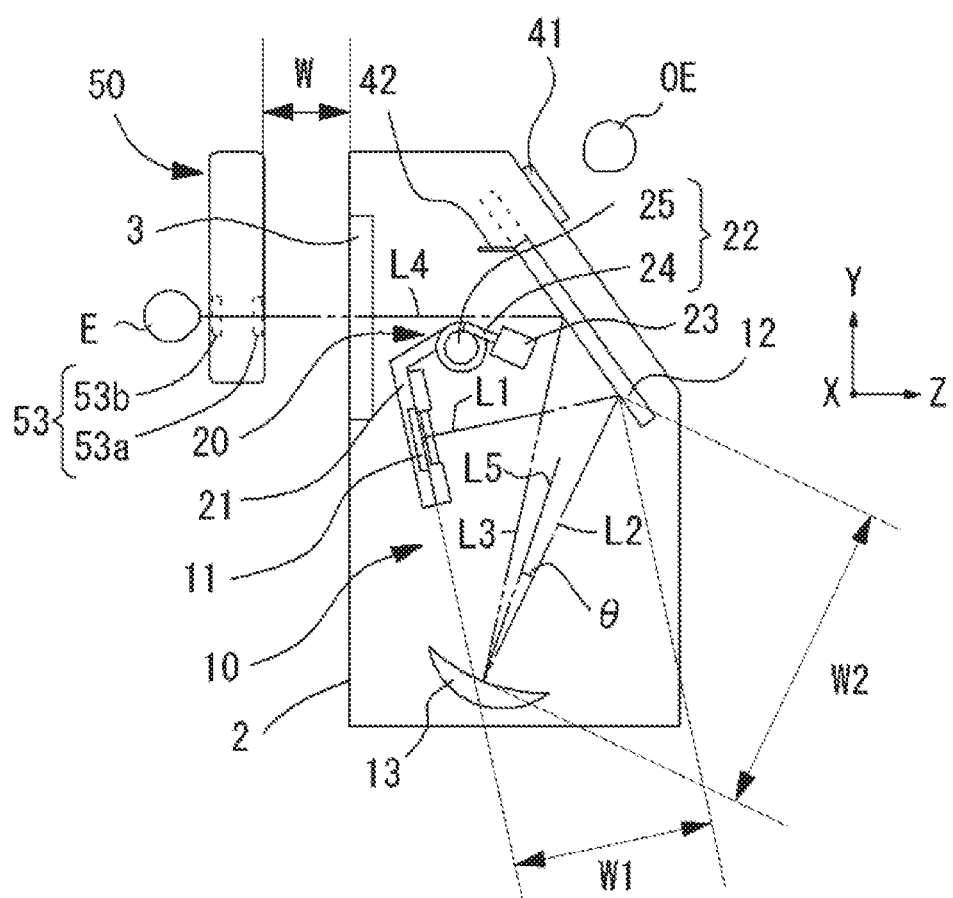
FIG. 4A illustrates optical disposition at the time of a far examination.
Figure 4B:
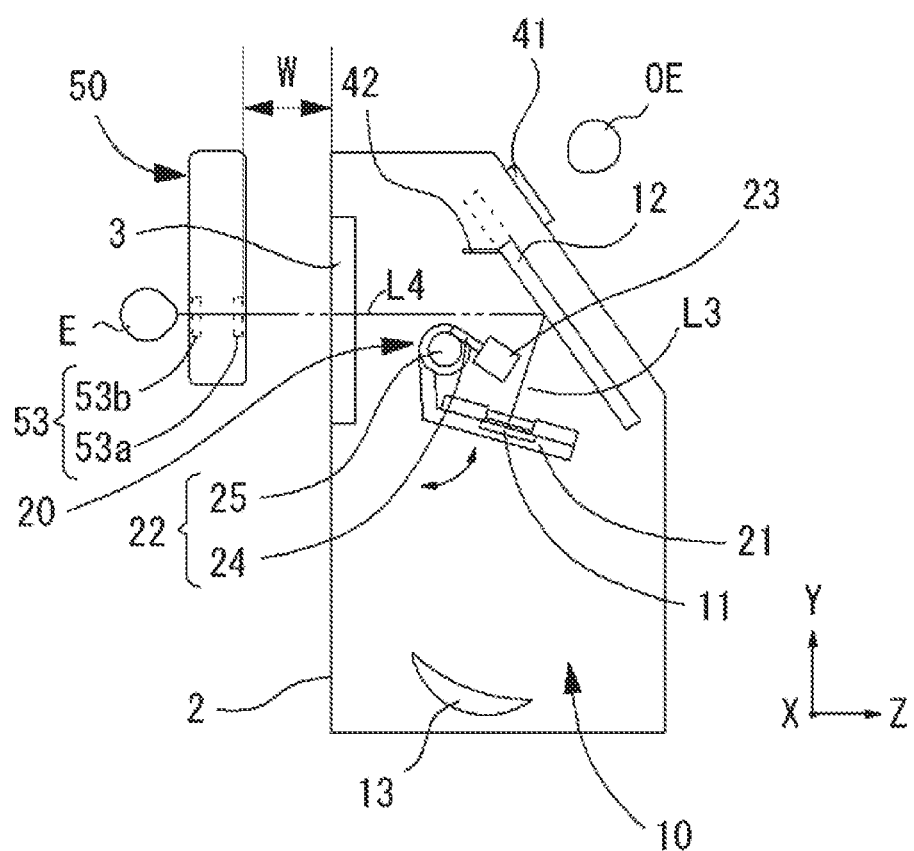
FIG. 4B illustrates optical disposition at the time of a near examination.

Hereinafter, the projection optical system 10 will be described. For example, FIGS. 4A and 4B are views of the projection optical system 10 when viewed from the left surface (arrow direction C1 in FIGS. 1A and 1B). FIG. 4A illustrates optical disposition at the time of a far examination. FIG. 4B illustrates optical disposition at the time of a near examination. For example, the projection optical system 10 has a visual target presenting portion and projects the target light flux emitted from the visual target presenting portion toward a subject eye E. For example, in the present example, a display (for example, display 11) is used as a visual target presenting portion. For example, the projection optical system 10 includes the display 11, the flat surface mirror 12, the concave mirror 13, a far-near switching portion 20, and the like.

For example, an examination visual target, such as a Landolt ring visual target or a fixation target, is displayed on the display 11. For example, the display on the display 11 is controlled by the control portion 80 which will be described later. For example, a liquid crystal display (LCD), an organic electroluminescence (EL), a plasma display or the like may be used as the display.

For example, at the time of the far examination illustrated in FIG. 4A, a screen of the display 11 is oriented toward a deep side of the housing 2, and the target light flux is emitted in the depth direction. In addition, the target light flux may be emitted in the horizontal direction (Z direction) from the display or may be emitted in an oblique direction (YZ direction). For example, at the time of the near examination illustrated in FIG. 43, the screen of the display 11 is oriented toward an upper side, and the target light flux is emitted upward. In addition, the target light flux may be emitted in the vertical direction (Y direction) from the display or may be emitted in the oblique direction (YZ direction). In this manner, the target light flux from the display 11 is projected toward the subject eye E.

For example, the flat surface mirror 12 reflects the target light flux from the display 11 and guides the target light flux to the concave mirror 13. In addition, for example, the flat surface mirror 12 reflects the target light flux from the display 11 and guides the target light flux to the subject eye E. For example, in the flat surface mirror 12, the mirror coating is performed only to the lower part (the solid line part of the flat surface mirror 12 in FIGS. 4A and 4B) and the mirror coating is not performed to the upper part (the dotted line part of the flat surface mirror 12 in FIGS. 4A and 4B).

Therefore, in the present example, the upper part of the flat surface mirror 12 is transparent. For example, at the time of the near examination, the optical distance from the display to the subject eye E is designed to be 40 cm. It is needless to say that the optical distance from the display 11 to the subject eye E is not limited to 40 cm at the time of the near examination, and may be different optical distances (for example, 20 cm, 30 cm, 50 cm, 60 cm, and the like). In addition, in the present example, the target light flux may be capable of being reflected, and is not limited to the configuration using the flat surface mirror. For example, a reflection member may be employed. In this case, for example, a configuration using a prism, a beam splitter, a half mirror, a total reflecting mirror or the like may be used.

For example, a tilt angle $\theta 2$ of the flat surface mirror 12 is designed to be 38°. It is needless to say that the tilt angle of the flat surface mirror 12 is not limited thereto. For example, the tilt angle of the flat surface mirror 12 may be any tilt angle between 30° and 40°. As the tilt angle of the flat surface mirror 12 is designed at any tilt angle between 30° and 40°, the subjective optometry apparatus can further save the space. In addition, the tilt angle of the flat surface mirror 12 may be a tilt angle with respect to the optical axis L4 through which the target light flux reflected by the flat surface mirror 12 is oriented toward the subject eye. For example, the tilt angle of the flat surface mirror 12 may be an angle formed by the optical axis through which the target light flux reflected by the flat surface mirror 12 is oriented toward the subject eye and the optical axis (axis in the normal direction of the reflection surface of the reflection member) of the flat surface mirror 12.

For example, the concave mirror 13 reflects the target light flux from the display 11 toward the flat surface mirror 12. For example, the concave mirror 13 sets the presentation distance of the examination visual target displayed on the display 11 as the far examination distance. For example, the focal distance of the concave mirror 13 is designed such that the optical distance from the display 11 to the subject eye E is 5 m. It is needless to say that the optical distance from the display 11 to the subject eye E is not limited to 5 m, and may be different optical distances (for example, 3 m, 4 m and the like). In the present example, for example, the focal distance of the concave mirror 13 is designed to be 637.5 mm. It is needless to say that the focal distance of the concave mirror 13 is not limited thereto. In addition, in the present example, the configuration is not limited to the configuration in which the concave mirror 13 is used. For example, the reflection member capable of reflecting the target light flux may be employed. In this case, for example, a configuration using a non-spherical surface mirror, free curved surface mirror, or the like is used may be employed. In addition, for example, the configuration in which the lens is used may be employed. In this case, for example, a configuration in which, when the target light flux is projected onto the subject eye E from the display 11 via the lens, the optical distance from the display 11 to the subject eye E is designed to be 5 m by the lens may be employed.

For example, at the time of the far examination illustrated in FIG. 4A, the target light flux is emitted from the display 11 and is projected onto the subject eye E of the examinee passing through the optical members in the order of the flat surface mirror 12, the concave mirror 13, and the flat surface mirror 12. In other words, when the target light flux emitted from the display 11 is incident on the flat surface mirror 12 through an optical axis L1, the target light flux is reflected in an optical axis L2 direction and is oriented toward the concave mirror 13. In addition, an incident angle θ of the target light flux emitted from the display 11 to the concave mirror 13 is designed to be 4.9°. It is needless to say that the incident angle is not limited to the above-described configuration, and may be equal to or less than 10°. In addition, in the present example, the incident angle θ is an angle formed by an optical axis L5 of the concave mirror 13 and the optical axis L2.

For example, in the present example, the distance W1+W2 from the display 11 to the concave mirror 13 at the time of the far examination is designed to be 555 mm. It is needless to say that the distance W1+W2 from the display 11 to the concave mirror 13 is not limited to the above-described configuration, and may be 540 mm to 570 mm or less. In addition, the distance W1+W2 from the display 11 to the concave mirror is a distance obtained by the distance W1 on the optical axis L1 until the target light flux emitted from the display 11 is incident on the flat surface mirror 12, and the distance W2 on the optical axis L2 until the target light flux reflected by the flat surface mirror 12 is incident on the concave mirror 13. In other words, a distance obtained by adding the distance W1 and the distance W2 is the distance W1+W2 from the display 11 to the concave mirror 13.

For example, when the target light flux is incident on the concave mirror 13, the target light flux is reflected in an optical axis L3 direction and is oriented toward the flat surface mirror 12. Furthermore, when the target light flux is incident on the flat surface mirror 12, the target light flux is reflected in an optical axis L4 direction and is projected onto the subject eye E of the examinee. In addition, for example, at the time of the near examination illustrated in FIG. 4B, the target light flux emitted from the display 11 and reflected to the flat surface mirror 12 is projected onto the subject eye E of the examinee. In other words, when the target light flux emitted from the display 11 is incident on the flat surface mirror 12 through the optical axis L3, the target light flux is reflected in the optical axis L4 direction and is projected onto the subject eye E of the examinee. For example, in this manner, the projection optical system 10 emits the target light flux from the inside of the housing 2 to the outside of the housing 2.

For example, the far-near switching portion 20 changes the position of the display 11 at the time of the far examination and the near examination. For example, the far-near switching portion 20 includes a holding portion 21, a gear 22, a motor 23, and the like. For example, the holding portion 21 holds the display 11. For example, the gear 22 has a worm portion 24 and a wheel portion 25. For example, the worm portion 24 and the wheel portion 25 are formed of gears that mesh with each other. For example, the motor 23 is connected to the worm portion 24, and the holding portion 21 is connected to the wheel portion 25. For example, the worm portion 24 rotates as the motor 23 is driven, and accordingly, the wheel portion 25 rotates in the arrow direction. Accordingly, it is possible to integrally move the display 11 together with the holding portion 21, and to switch the presentation position of the examination visual target displayed on the screen of the display 11 at the time of the far examination and the near examination. In addition, the gear 22 and the motor 23 are disposed on the side wall of the housing 2 and are disposed at positions which do not obstruct the target light flux oriented from the display 11 toward the subject eye E.

In addition, in the present example, an example in which the optical axis L3 and the optical axis L4 of the projection optical system 10 are coaxial at the time of the far examination and the near examination has been described as an example, but the present invention is not limited thereto. For example, in the present example, the target light flux may be capable of being guided to the subject eye E, and may be configured to pass through different optical paths at the time of the far examination and the near examination.

<Observation Unit>

Figure 5:
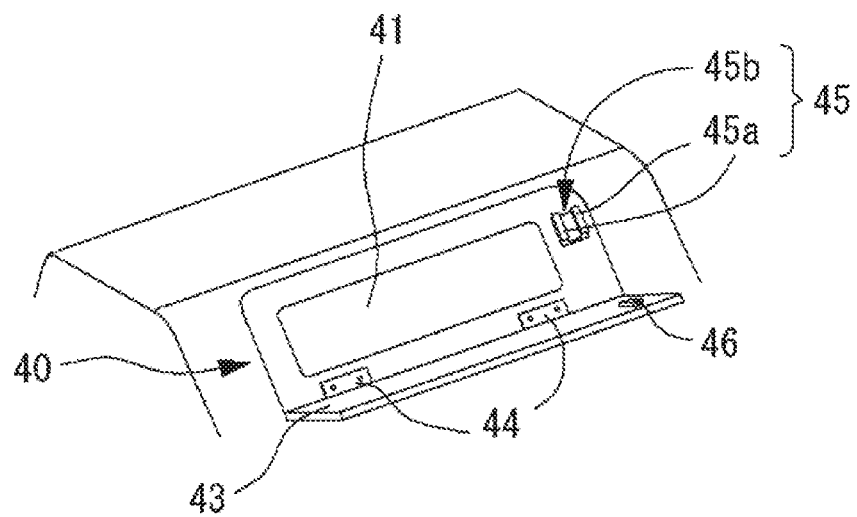
FIG. 5 is a view for describing an observation unit.

Next, the observation unit 40 will be described. FIG. 5 is a view for describing the observation unit. For example, the observation unit 40 in the present example is used for observing the positional relationship between the eye refractive power measurement unit 50 and the subject eye E which will described later via the presentation window 3. For example, in the present example, the observation unit 40 includes the observation window 41, a shielding portion 42, a cover 43, a detector (detection means) 45, and the like. In addition, the observation unit 40 may be configured to include at least the observation window 41.

For example, the observation window 41 is used for observing the positional relationship between the eye refractive power measurement unit 50 and the subject eye E via the presentation window 3 from the outside of the housing 2. For example, the observation window 41 in the present example is disposed at a position where it is possible to confirm a pupil position of the subject eye E from an examiner eye OE. For example, in a case where the examiner looks into the observation window 41, the flat surface mirror 12 is formed to be transparent in a region through which the line of sight of the examiner passes such that the line of sight of the examiner is not blocked by the flat surface mirror 12. For example, the shielding portion 42 suppresses entrance of the target light flux from the projection optical system 10 into the observation window 41. For example, in the present example, the shielding portion 42 is disposed at the boundary between the transparent portion and the mirror portion of the flat surface mirror 12.

For example, the cover 43 is fixed to the housing 2 by a hinge 44, and can be opened and closed with respect to the observation window 41. For example, the cover 43 can be opened and closed as the examiner pushes and pulls a knob (not illustrated).

For example, the detector 45 detects the opening and closing of the cover 43 in the observation unit 40. For example, the detector 45 is configured using an optical sensor, such as a photo interrupter. In other words, the detector 45 in the present example has a projection portion 45a in which the light emitting element and the light receiving element face each other, and a protrusion portion 46 provided on the cover 43 is fitted into a recess portion 45b. For example, the detector 45 detects that the cover is in a closed state when the light from the light emitting element is shielded by making the protrusion portion 46 fitted into the recess portion 45b. In addition, for example, the detector 45 detects that the cover is in an opened state when the protrusion portion 46 is separated from the recess portion 45b and the light from the light emitting element is received by the light receiving element.

<Eye Refractive Power Measurement Unit>

Hereinafter, the eye refractive power measurement unit 50 will be described. For example, the eye refractive power measurement unit 50 is close to the housing 2 (refer to FIGS. 4A and 49). For example, in the present example, a distance W (refer to FIGS. 4A and 4B) from the examination window 53 in the eye refractive power measurement unit 50 to the presentation window 3 disposed in the housing 2 is designed to be 66 mm. For example, in the present example, the viewing angle from the examination window 53 is designed to be 40°. For example, the optometric window 53 includes an optometric window 53a disposed on the housing 2 side and an optometric window 53b disposed on the subject eye E side. In the present example, the distance W from the optometric window 53a disposed on the housing 2 side to the presentation window 3 disposed on the housing 2 side is designed to be 66 mm. In addition, the distance W from the examination window 53a to the presentation window 3 is not limited to the present example. For example, the distance W may be equal to or less than 180 mm.

For example, in a case where the distance W is shorter than a head length of the examiner, it is not possible for the examiner to insert the head between the eye refractive power measurement unit 50 and the housing 2, and thus, it becomes difficult to observe the positional relationship between the eye refractive power measurement unit 50 and the subject eye E. Therefore, in a case where the distance w is shorter than the head length of the examiner, it is possible to effectively use the observation window 41.

Figure 6:
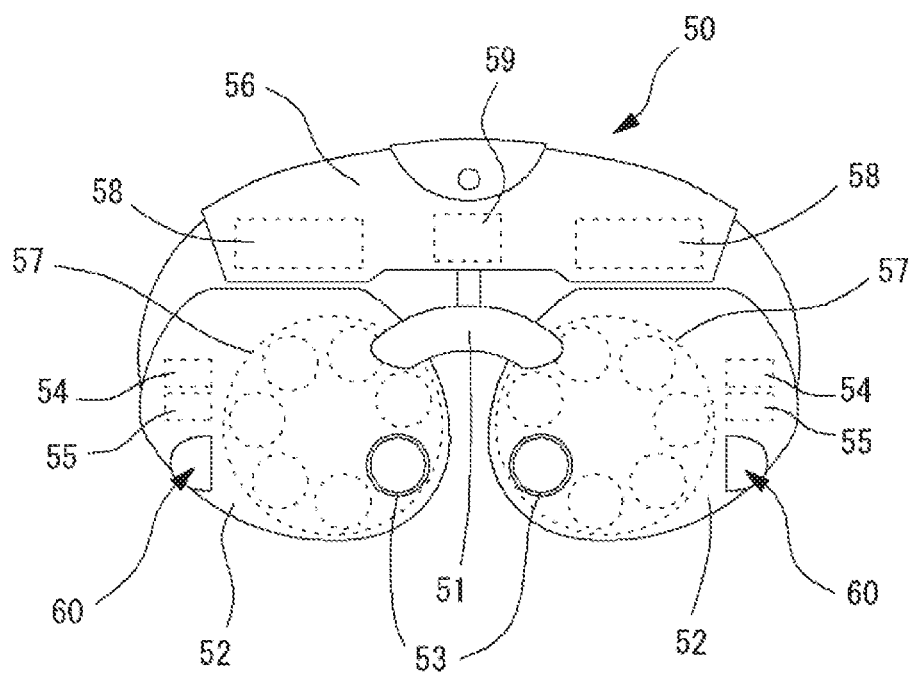
FIG. 6 is a view illustrating an eye refractive power measurement unit.

For example, FIG. 6 is a view illustrating the eye refractive power measurement unit 50. For example, the eye refractive power measurement unit 50 includes a forehead rest 51, a pair of left and right lens chamber units 52, the examination window 53, a driving portion 54, a driving portion 55, a moving unit 56, a cornea position aiming optical system 60 and the like. For example, the forehead rest 51 abuts against the forehead of the examinee and is used for keeping the distance between the subject eye E and the eye refractive power measurement unit 50 constant.

For example, the lens chamber unit 52 switches and disposes the optical element in the examination window 53. For example, a lens disk 57 is provided on the inside of the lens chamber unit 52. The lens disk 57 disposes a large number of optical elements (a spherical lens, a cylindrical lens, a dispersing prism, and the like) on the same circumference. For example, the lens disk 57 is rotationally controlled by the driving portion 54 (an actuator and the like). Accordingly, the optical element desired by the examiner is disposed in the examination window 53. For example, the optical element disposed in the examination window 53 is rotationally controlled by the driving portion 55 (a motor, a solenoid, and the like). Accordingly, the optical element is disposed in the examination window 53 by a rotation angle desired by the examiner.

For example, the lens disk 57 is configured of one lens disk or a plurality of lens disks. For example, in a case where the plurality of lens disks (lens disk groups) are provided, a driving portion that corresponds to each lens disk is provided. For example, each lens disk of the lens disk group includes an opening (or a OD lens) and a plurality of optical elements. As a type of each of the lens disks, a spherical lens disk having a plurality of spherical lenses with different frequencies, a cylindrical lens disk having a plurality of cylindrical lenses with different frequencies, and an auxiliary lens disk are representative. Further, the lens disk in the present example includes a positioning lens with a cross hatched line. For example, at least one of a red filter and a green filter, a prism, a cross cylinder lens, a polarizing plate, a Maddox lens, and an autocross cylinder lens is disposed on the auxiliary lens disk. In addition, for the detailed configuration of the lens disk, it is desired to refer to JP-A-2007-68574 and JP-A-2011-72431.

For example, the moving unit 56 adjusts an interval between the lens chamber units 52. For example, the interval between the left and right lens chamber units is adjusted by the driving portion 58 having a slide mechanism. Accordingly, the interval of the examination window 53 can be changed according to a pupillary distance (PD) of the examinee. Further, the moving unit 56 adjusts a convergence angle (inside angle) of the left and right lens chamber units. For example, the convergence angle of the left and right eye refractive power measurement units is adjusted by a driving portion 59 having a convergence mechanism. In addition, for the detailed configuration of the moving unit, it is desired to refer to JP-A-2004-329345.

In addition, the eye refractive power measurement unit 50 is not limited to the above-described configuration. For example, the eye refractive power measurement unit 50 may be configured to change the optical characteristics (for example, at least any one of a spherical power, a cylindrical power, a cylindrical axis, polarization characteristics, and the aberration amount) of the target light flux. For example, as a configuration in which the optical characteristics of the target light flux is changed, a configuration in which an optical element is controlled may be employed. For example, a configuration using a wavefront modulation element may be employed.

<Control Portion>

Figure 7:
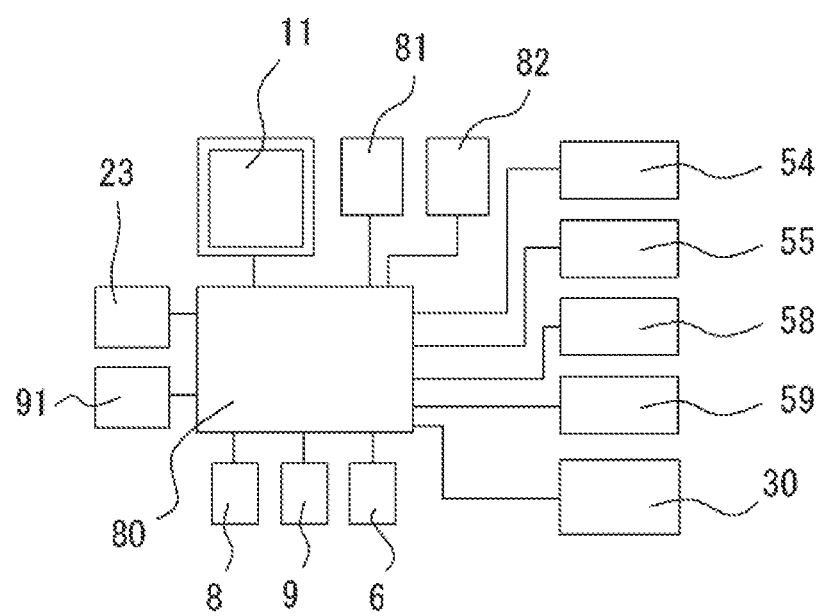
FIG. 7 is a schematic configuration view of a control system in the subjective optometry apparatus.

For example, FIG. 7 is a schematic configuration view of a control system in the subjective optometry apparatus 1. For example, the first operation portion 8, the second operation portion 9, the display 11, the detector 45, a controller 81, a non-volatile memory 82, a light source 91, and the like are connected to the control portion 80. In addition, for example, the motor 30 included in the moving unit 6, the motor 23 included in the far-near switching portion 20, and the driving portion (driving portions 54, 55, 58, and 59) of each member of the eye refractive power measurement unit 50, and the like, are connected to the control portion 80.

For example, the control portion 80 includes a CPU (processor), a RAM, a ROM, and the like. For example, the CPU controls each member of the subjective optometry apparatus 1. For example, the RAM temporarily stores various pieces of information. For example, various programs for controlling the operation of the subjective optometry apparatus 1, examination visual target data, and the like, are stored in the ROM. Meanwhile, the control portion 80 may be configured with a plurality of control portions (that is, a plurality of processors).

For example, the controller 81 is used when switching the display of the display 11 in the projection optical system 10, disposition of the optical elements in the eye refractive power measurement unit 50, and the like. For example, a signal input from the controller 81 is input to the control portion 80 via a cable (not illustrated). In addition, in the present example, the signal from the controller 81 may be input to the control portion 80 via wireless communication, such as infrared rays.

For example, the non-volatile memory 82 is a non-fugitive storage capable of holding stored contents even when the supply of power is stopped. For example, as the non-volatile memory 82, a hard disk drive, a flash ROM, and a USB memory, or the like can be used. For example, the non-volatile memory 82 stores multiple pieces of the examination visual target data, such as a Landolt ring visual target (for example, visual target data of visual acuity values 0.1 to 2.0).

For example, in the present example, the control portion 80 switches a measurement mode of the subjective optometry apparatus 1 based on the detection result of the detector 45. For example, in the present example, the control portion 80 automatically switches the measurement mode in conjunction with the opening and closing of the cover 43. For example, when the detector 45 detects that the cover 43 is opened, the control portion 80 sets the measurement mode to a second mode for confirming the pupil position of the examinee. In addition, for example, when the detector 45 detects that the cover 43 is closed, the control portion 80 sets the measurement mode to a first mode for subjectively examining the examinee. In addition, in the present example, the configuration in which the measurement mode is automatically switched in conjunction with the opening and closing of the cover 43 is employed, but the present invention is not limited thereto. For example, the switching of the measurement mode may be performed manually by the examiner. In this case, a signal for switching the measurement mode may be input to the control portion 80 by using the controller 81 which will be described later.

<Examination Operation>

An examination operation of the subjective optometry apparatus 1 having the above-described configuration will be described. For example, the examiner operates the first operation portion 8 to lower the eye refractive power measurement unit 50 to the examination position illustrated in FIG. 8. For example, when the first operation portion 8 is operated, the control portion 80 drives the motor 30. For example, by driving the motor 30, the eye refractive power measurement unit 50 is lowered toward the examination position. For example, when the eye refractive power measurement unit 50 is moved to the examination position by driving the motor 30, the block 32 and the block receiver 36 come into contact with each other and the lowering of the eye refractive power measurement unit 50 is stopped. In addition, together with the stop of the eye refractive power measurement unit 50, the movement of the supporting member 85 is started, and when the supporting member 85 is moved to a predetermined position, the driving of the motor 30 is stopped. Accordingly, as illustrated in FIG. 8, the movement of the eye refractive power measurement unit 50 to the examination position is completed, and the subjective examination using the eye refractive power measurement unit 50 becomes possible.

As described above, the eye refractive power measurement unit 50 moves to the examination position. Next, for example, the examiner measures the PD of the examinee in advance before performing the subjective examination, and inputs the measured PD in the subjective optometry apparatus 1. Accordingly, the control portion 80 drives the driving portion 58, adjusts the interval between the left and right lens chamber units 52, and changes the interval of the examination window 53 in accordance with the PD of the subject eye. For example, the control portion 80 performs adjustment such that the distance in the horizontal direction (X direction) between the optical axes of the left and right examination windows 53 becomes the same as the PD. In addition, in the present example, the expression "the same" also includes being substantially the same.

Next, the examiner instructs the examinee to look into the examination window 53. Here, for example, the examiner opens the cover 43 for confirming a pupillary distance PD of the subject eye E. At this time, when the detector 45 detects that the cover 43 is opened, the control portion 80 switches the measurement mode to the second mode for confirming the pupil position of the examinee.

For example, the examiner adjusts the interval between the left and right lens chamber units 52 by operating the controller 81 as necessary. Next, in order to confirm a cornea apex position of the subject eye E, the examiner performs positioning of the subject eye E with respect to the eye refractive power measurement unit 50 by using the cornea position aiming optical system 60.

For example, when the positioning of the subject eye E to the eye refractive power measurement unit 50 is completed, the examiner closes the cover 43 and starts the subjective examination. At this time, the detector 45 detects that the cover 43 is closed, and the control portion 80 switches the measurement mode to the first mode for subjectively examining the examinee.

In addition, for example, in a case of performing the far examination (refer to FIG. 4A), the control portion 80 turns on the display 11. For example, from the display 11 held by the holding portion 21, the target light flux is emitted toward the flat surface mirror 12. The target light flux is reflected by the flat surface mirror 12 and the concave mirror 13, respectively, and guided to the subject eye E via the flat surface mirror 12 again. In addition, for example, in a case of performing the near examination (refer to FIG. 4B), the display 11 moves together with the holding portion 21 and is disposed to be close to the subject eye E (for example, a distance of 40 cm away). From the display 11, the target light flux is emitted toward the flat surface mirror 12. The target light flux is reflected by the flat surface mirror 12 and guided to the subject eye E.

For example, at the time of the far examination and the near examination, the examiner operates the controller 81 and displays the examination visual target on the screen of the display 11. Corresponding to the input signal from the controller 81, the control portion 80 calls the corresponding examination visual target data from the non-volatile memory 82 and controls the display on the display 11. The examination visual target displayed on the display 11 is presented to the subject eye E of the examinee via the examination window 53 in the eye refractive power measurement unit 50 and the presentation window 3.

For example, the examiner asks the examinee about appearance of the examination visual target while switching the examination visual target. For example, the visual target is switched to a visual target having a visual acuity value higher by one step in a case where the answer of the examinee is a correct answer. In addition, for example, the visual target is switched to a visual target having a visual acuity value lower by one step in a case where the answer of the examinee is an incorrect answer. By performing the visual function examination in this manner, the examiner can acquire the optical characteristics (for example, spherical power S, cylindrical surface power C, astigmatic axis angle A, and the like) of the subject eye E.

For example, when the far examination or the near examination is completed, the examiner performs provisional frame examination with respect to the subject eye E. For example, the examiner operates an upper switch 8a of the first operation portion 8 to raise the eye refractive power measurement unit 50 to the retracted position illustrated in FIGS. 1A and 1B. For example, when the upper switch 8a of the first operation portion 8 is operated, the control portion 80 drives the motor 30. In addition, for example, in a case of moving the eye refractive power measurement unit 50 to the retracted position, the control portion 80 rotates the motor 30 in a rotation direction opposite to the rotation direction of the motor 30 in a case of moving the eye refractive power measurement unit 50 to the examination position.

For example, when the movement of the eye refractive power measurement unit 50 to the retracted position is completed, the examiner mounts a provisional frame (a trial frame or a test frame) on the examinee and confirms the mounting feeling while exchanging lenses (trial lenses) having various degrees.

As described above, for example, in the present example, in the subjective optometry apparatus, in a case of using the eye refractive power measurement unit, the first distance from the presentation window to the eye refractive power measurement unit in the optical path through which the target light flux from the visual target presenting portion is projected onto the subject eye is equal to or less than 180 mm (in the present example, 66 mm), According to this, it is possible to save the space for the subjective optometry apparatus, and to perform a highly accurate subjective examination even in a case of the subjective optometry apparatus in which the eye refractive power measurement unit and the housing are integrated with each other.

Further, in the present example, the visual target presenting portion and the optical member may be disposed such that the second distance from the visual target presenting portion to the optical member in the optical path is any distance between 540 mm and 570 mm (in the present example, 555 mm), in order to enable to subjectively measure the optical characteristics of the subject eye with the first distance. Accordingly, it is possible to save the space for the subjective optometry apparatus and to perform a highly accurate subjective examination.

In addition, in the present example, for example, the optical member may be a concave mirror, and the incident angle of the target light flux to the concave mirror may be equal to or less than 10° (in the present example, 4.9°). Accordingly, distortion or aberration due to the concave mirror can be suppressed, and a highly accurate subjective examination can be performed.

Further, for example, in the present example, the presentation window may have the size of 130 mm or more in the horizontal direction and the size of 50 mm or more in the vertical direction (in the present example, the size in the horizontal direction is 184 mm and the size in the vertical direction is 99 mm), in order to enable to subjectively measure the optical characteristics of the subject eye with the first distance. With such a configuration, in a case of an integrated subjective optometry apparatus, when the examinee observes the visual target presenting portion through the optometric window, the narrowing of the viewing angle when looking into the optometric window is suppressed, and preferably, the subjective examination can be performed. In addition, when the visual target presenting portion is observed through the optometric window, as a frame or the like of the presentation window is seen, the action of an adjustment force of the subject eye can be suppressed, and a highly accurate subjective examination can be performed.

Further, for example, in the present example, the presentation window may have the size of 270 mm or less in the horizontal direction and the size of 190 mm or less in the vertical direction (in the present example, the size in the horizontal direction is 184 mm and the size in the vertical direction is 99 mm), in order to enable to subjectively measure the optical characteristics of the subject eye with the first distance. With such a configuration, in a case of an integrated subjective optometry apparatus, when the visual target presenting portion is observed through the optometric window, as the disturbance light reflected by the presentation window is guided to the subject eye and the disturbance light enters the housing, difficulty of confirming of the visual target can be suppressed and a highly accurate subjective examination can be performed.

In addition, for example, in the present example, the subjective optometry apparatus may have: moving means that includes driving means for moving the position of the eye refractive power measurement unit, and enables move the eye refractive power measurement unit to move between the examination position in front of the subject eye and the retracted position by driving the driving means; and control means that controls the moving means to move the eye refractive power measurement unit between the examination position in front of the subject eye and the retracted position by driving the driving means. For example, the eye refractive power measurement unit can be easily moved by automatically moving the eye refractive power measurement unit between the examination position in front of the subject eye and the retracted position.

In addition, for example, in the present example, the moving means may be configured to enable the eye refractive power measurement unit to move to the retracted position where is above the examination position. Accordingly, since the eye refractive power measurement unit can be retracted without crossing the face of the examinee, it is possible to provide a subjective optometry apparatus that can further suppress excessive contact.

In addition, in the present example, when the subjective optometry apparatus 1 is moved, a fixing portion for fixing the display 11 may be provided. For example, the fixing portion may be operated by the examiner from the outside of the housing 2. As an example, the fixing portion is operated by the examiner, and the display 11 is fixed. For example, a screw or the like can be used as the fixing portion. For example, the display 11 may be provided with a screw receiver, and the screw may be fitted into the screw receiver of the display as the examiner turns the screw, and the movement of the display 11 may be restricted. Accordingly, the movement of the display 11 that can be moved at the time of the far examination and the near examination can be restricted, and failure can be suppressed. In other words, since the display 11 of the subjective optometry apparatus 1 according to the present example has a movable configuration, when the subjective optometry apparatus 1 is moved, the display 11 moves and comes into contact with other members, and accordingly, failure can be suppressed.

In addition, in the present example, when the subjective optometry apparatus 1 is moved, a handle for holding the subjective optometry apparatus 1 may be provided. For example, the handle may be provided at a bottom portion of the subjective optometry apparatus 1. For example, the handle may be provided on each of the left and right sides of the housing 2 so as to be movable with the left and right hands of the examiner. Further, for example, a placement portion may be connected to the handle part in order to dispose the controller 81.

In addition, in the present example, a moth-eye film may be provided on a screen of the display 11. Accordingly, reflection on the screen of the display 11 can be suppressed, and a highly accurate examination can be performed. In addition, as a configuration provided on the screen of the display 11, the present invention is not limited to the moth-eye film. For example, a film or a coating that can suppress the reflection on the screen of the display 11 may be performed.

REFERENCE SIGNS LIST 1 subjective optometry apparatus
2 housing
3 presentation window
4 holding unit
5 connecting portion
6 moving unit
7 shaft
8 first operation portion
9 second operation portion
10 projection optical system
11 display
30 driving portion
31 base
32 block
35 holding arm
36 block receiver
38 supporting member
39 block receiver
40 observation unit
50 eye refractive power measurement unit
53 examination window
60 cornea position aiming optical system
80 control portion
85 supporting member
90 elbow rest

The invention claimed is:

1. A subjective optometry apparatus comprising:
a projection optical system that includes a visual target presenting portion which emits a target light flux and an optical member which guides an image of the target light flux to a subject eye so as to have an optically predetermined examination distance, that causes the target light flux emitted from the visual target presenting portion to be incident on the optical member along an optical axis that deviates from an optical axis of the optical member, and that projects the target light flux toward the subject eye;
a housing that accommodates the projection optical system;
a presentation window provided on the housing to emit the target light flux from an inside of the housing to an outside of the housing therethrough;
an eye refractive power measurement unit provided outside the housing to change optical characteristics of the target light flux emitted from the housing; and
holding means that integrally connects the housing and the eye refractive power measurement unit to hold the eye refractive power measurement unit,
wherein the target light flux through the eye refractive power measurement unit is projected onto the subject eye to subjectively measure optical characteristics of the subject eye, and
in a case of using the eye refractive power measurement unit, a first distance from the presentation window to the eye refractive power measurement unit in an optical path through which the target light flux from the visual target presenting portion is projected onto the subject eye is equal to or less than 180 mm,
wherein the subject optometry apparatus further comprises:
moving means that includes driving means for moving a position of the eye refractive power measurement unit, and that enables to the eye refractive power measurement unit to move between an examination position in front of the subject eye and a retracted position by driving the driving means; and
control means that controls the moving means to move the eye refractive power measurement unit between the examination position in front of the subject eye and the retracted position by driving the driving means; and
wherein the moving means enables the eye refractive power measurement unit to move to the retracted position vertically upwards relative the projection optical system accommodated in the housing and above the examination position, and the eye refractive power measurement unit in the retracted position is in a state of being raised above the housing.

2. The subjective optometry apparatus according to claim 1,
wherein the visual target presenting portion and the optical member are disposed such that a second distance from the visual target presenting portion to the optical member in the optical path is any distance between 540 mm and 570 mm, in order to enable to subjectively measure the optical characteristics of the subject eye with the first distance.

3. The subjective optometry apparatus according to claim 1
wherein the optical member is a concave mirror, and
an incident angle of the optical axis of target light flux on the optical member relative to the optical axis of the concave mirror is equal to or less than 10°.

4. The subjective optometry apparatus according to claim 1, comprising a housing and wherein, the presentation window is contained within the housing and has a size of 130 mm or more in a horizontal direction and a size of 50 mm or more in a vertical direction, in order to enable to subjectively measure the optical characteristics of the subject eye with the first distance.

5. The subjective optometry apparatus according to claim 1
wherein, the presentation window has a size within a range of 130 mm to 270 mm in a horizontal direction and a size within a range of 50 mm to 190 mm in a vertical direction, in order to enable to subjectively measure the optical characteristics of the subject eye with the first distance.

6. The subjective optometry apparatus according to claim 1,
wherein the optical member is a concave mirror, and
the projection optical system has a reflection member that reflects the target light flux emitted from the visual target presenting portion toward the concave mirror, and guides the target light flux reflected by the concave mirror from the inside of the housing to the outside of the housing.

7. The subjective optometry apparatus according to claim 1,
wherein the holding means integrally connects the eye refractive power measurement unit to an upper surface of the housing.

8. The subjective optometry apparatus according to claim 1,
wherein in a case of using the eye refractive power measurement unit, an examination window of the eye refractive power measurement unit and the presentation window are disposed to face each other.

9. The subjective optometry apparatus according to claim 1, wherein the first distance is equal to or greater than 10 mm.

10. The subjective optometry apparatus according to claim 1, wherein the projection optical system comprises a far-near switching portion configured to physically change a position of the visual target presenting portion between a far examination position and a near examination position.

11. A subjective optometry apparatus comprising:
a projection optical system that includes a visual target presenting portion which emits a target light flux and an optical member which guides an image of the target light flux to a subject eye so as to have an optically predetermined examination distance, that causes the target light flux emitted from the visual target presenting portion to be incident on the optical member along an optical axis that deviates from an optical axis of the optical member, and that projects the target light flux toward the subject eye;
a housing that accommodates the projection optical system;
a presentation window provided on the housing to emit the target light flux from an inside of the housing to an outside of the housing therethrough;
an eye refractive power measurement unit provided outside the housing to change optical characteristics of the target light flux emitted from the housing; and
holding means that integrally connects the housing and the eye refractive power measurement unit to hold the eye refractive power measurement unit,
wherein the target light flux through the eye refractive power measurement unit is projected onto the subject eye to subjectively measure optical characteristics of the subject eye, and
in a case of using the eye refractive power measurement unit, a first distance from the presentation window to the eye refractive power measurement unit in an optical path through which the target light flux from the visual target presenting portion is projected onto the subject eye is equal to or less than 180 mm, and
wherein the holding means integrally connects the eye refractive power measurement unit to an upper surface of the housing accommodating the projection optical system, such that when the eye refractive power measurement unit is moved to a retracted position, the eye refractive power measurement unit is raised above the housing.

* * * * *